United States Patent
Li et al.

(10) Patent No.: US 10,177,325 B2
(45) Date of Patent: Jan. 8, 2019

(54) LIGHT EMITTING HYBRID SEMICONDUCTORS BASED ON IB-VII BINARY COMPOUNDS

(71) Applicant: Rutgers, The State University of New Jersey, New Brunswick, NJ (US)

(72) Inventors: Jing Li, Cranbury, NJ (US); Xiao Zhang, Piscataway, NJ (US); George Z. Wei, North Brunswick, NJ (US); Wei Liu, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 176 days.

(21) Appl. No.: 14/896,870

(22) PCT Filed: Jun. 13, 2014

(86) PCT No.: PCT/US2014/042340
§ 371 (c)(1),
(2) Date: Dec. 8, 2015

(87) PCT Pub. No.: WO2014/201377
PCT Pub. Date: Dec. 18, 2014

(65) Prior Publication Data
US 2016/0133839 A1 May 12, 2016

Related U.S. Application Data

(60) Provisional application No. 61/834,955, filed on Jun. 14, 2013.

(51) Int. Cl.
*C09K 11/00* (2006.01)
*C09K 11/58* (2006.01)
(Continued)

(52) U.S. Cl.
CPC .............. *H01L 51/009* (2013.01); *C07F 1/08* (2013.01); *C07F 1/10* (2013.01); *C07F 1/12* (2013.01);
(Continued)

(58) Field of Classification Search
CPC . H10L 51/009; H10L 51/0091; H10L 33/502; C09K 11/06; C09K 2211/188; C07F 1/08; C07F 1/10; C07F 1/12
See application file for complete search history.

(56) References Cited

U.S. PATENT DOCUMENTS 3,086,973 A   4/1963   Nyholm et al.
2008/0199731 A1   8/2008   Vogler et al.

FOREIGN PATENT DOCUMENTS

CN   101696218   4/2010
CN   102459289 A   5/2012
(Continued)

OTHER PUBLICATIONS

Lee et al, "Structures and Photoluminescnce Propeties of 2-Dimensional Copper(I)-Halide Complexes Constructed by Rhomboid Cu2X2 (X=I and Br) Uits and Dipyridyl Ligand", Bull. Korean Chem. Soc. 2008, vol. 29, No. 8, pp. 1811-1814.*

(Continued)

*Primary Examiner* — C Melissa Koslow
(74) *Attorney, Agent, or Firm* — Fox Rothschild LLP (57) ABSTRACT

Inorganic-organic hybrid IB-VII semiconductor compounds, in which a Group IB transition metal halide salt is coordinated with an organic heteroaromatic ligand, wherein at least one ring atom of said heteroaromatic ligand is a heteroatom independently selected from N, O and S and the Group IB metal of the halide salt is coordinated to a ring heteroatom. Also disclosed are semiconductor and light emitting devices comprising these materials, including light (Continued)

emitting diodes, and methods of preparing these materials and devices.

17 Claims, 5 Drawing Sheets (51) Int. Cl.
H01L 33/26 (2010.01)
H01L 51/00 (2006.01)
C07F 1/10 (2006.01)
H01L 33/50 (2010.01)
C07F 1/12 (2006.01)
C09K 11/06 (2006.01)
C07F 1/08 (2006.01)
H01L 51/50 (2006.01)

(52) U.S. Cl.
CPC ............ *C09K 11/06* (2013.01); *H01L 33/502* (2013.01); *H01L 51/0091* (2013.01); *C09K 2211/1022* (2013.01); *C09K 2211/1029* (2013.01); *C09K 2211/1044* (2013.01); *C09K 2211/188* (2013.01); *H01L 51/5016* (2013.01)

(56) References Cited

FOREIGN PATENT DOCUMENTS

| EP | 0532861 A1 | 3/1993 |
| EP | 2210882 | 7/2010 |
| GB | 2160524 | * 12/1985 |
| JP | H10-312073 A | 11/1998 |
| JP | 2012-530762 A | 12/2012 |
| WO | 2012/156378 A1 | 11/2012 |
| WO | 2013/017675 A1 | 2/2013 |

OTHER PUBLICATIONS

Muthu et al, Photoluminescent coordination polymers of d10 metals with 4,4'-dipyridylsulfide (Dps), Inorganica Chimica Acta 358, Oct. 2004, pp. 595-605.*
Chemical Abstract citation 78:148044, abstract for Hardt et al, "Fluorescenece-thermochromic compounds of copper(I) iodide with ethyl and aminopyridines", Zeitschrift fuer Anorganische und Allemeine Chemie, 1973, 391(1), 23-30.*
Dyason et al, Lewis Base Adducts of Group 11 Metal Compounds. 15. Structural Studies of Mononuclear Addcuts of Copper(I) Halides with Pyridine Bases of Stoichiometry XCuL2,3. Inorg. Chem. 1985, 23, pp. 1957-1960.*
Chemical Abstract citation 129:224927 abstract for Jones et al, "Gold(I) complexes with amine ligands. Part 2. Methylpyridine complexes of gold(I)", Zeitschrft fuer Naturforschung, B: Chemical Sciences, 53(7), 1988, pp. 653-662.*
Chemical Abstract citation 153:495500 abstract for Woelper et al, "A sinlpe system with many structural variants: a rexamination of amino(halogenidosilver(I) complexes", Zeitschrft fuer Naturforschung, B: A Journal of Chemical Sciences, 65(6), 2010, pp. 647-673.*
Robenbeck et al, "Three-Dimensional Copper(I) Halide Based Coordination Networks with Asymmetrically Substituted Bridging N-Donor Ligands", Z. Naturforsch vol. 54, No. 12, pp. 1510-1516, 1999.*
Lee, S. et al.: "Structures and Photoluminiescence Properties of 2-Dimensional Cooper(I)-Halide Complexes Constructed by Rhomboid Cu2X2 (X=I and Br) Units and Dipyridyl Ligand", Bull. Korean Chem. Soc. 2008, vol. 29, No. 9, pp. 1811-1814, [online], [retrieved on Sep. 12, 2014]. Retrieved from the Internet: <URL: http://pdf.easechem.com/pdf/32/cdff9bbd-68d8-4220-a849-10f445c63ffe.pdf>: p. 1811, paragraphs 1-3, figure 1; p. 1812, figure 2, full paragraph 1.
Graham P. et al.: "Coordination Polymers of Cooper(I) Halides", (abstract), Inorganic Chemistry 2000, 39 (22) pp. 5121-5132, [online], [retrieved on Sep. 16, 2014]. Retrieved from the Internet: <URL : http://pubs.acs.org/doi/abs/10.1021/ic0005341>; abstract.
Cariati, et al: "X-ray Structures and Emissive and Second-Order Nonlinear Optical Properties of Two Inorganic-Organic Polymeric Adducts of CuI with 4-Acetylpyridine. The Role of Both "Intrastrang" Charge Transfers and Structural Motifs on the Nonlinear Optical Response of Cu(I) Polymeric Adducts with Pseudoaromatic n1-Nitrogen Donor Ligants", 2002, Chem. Mater, vol. 14, pp. 5116-5123.
Etaiw, et al: "Structural Influence of the Ligand Geometry on Construction of Coordination Polymers Formed from Silver(I) Chloride Ribbons and Bipodal Nitrogen Donor Ligands", 2010, Journal of Inorganic and Organometallic Polymers and Materials, vol. 20, No. 4, pp. 684-691.
Jeb, et al: Synthesis, Crystal Structure, Thermal and Luminescence Properties of CuX(2,3-dimethylpyrazine) (X=Cl, Br, I) Coordination Polymers, 2007, Dalton Transactons, pp. 2263-2270.
Kitagawa, et al: "Effect of Substituents on the Charge Transfer Band of Cooper(I) Complexes with 4-Monosubstituted Pyridines", 1982, Inorganica Chimica Acta, vol. 59, No. 2, pp. 219-223.
Chen et al: "Solvent Effects on the Assembly of [Cu2I2]- or [Cu4I4]-Based Coordination Polymers: Isolation, Structures, and Luminescent Properties", 2008, Crystal Growth & Design, vol. 8, No. 10, pp. 3810,3816.
Baillie, et al: "Coordination Complexes of Functionalized Pyrazines with Metal Ions: Reagents for the Controlled Reelase of Flavourant Molecules at Elevated Temperatures", 2006, Flavour and Fragrance Journal, vol. 21, No. 2, pp. 202-206.
Blake, et al: "Topological Isomerism in Coordination of Polymers" 2001, Chemical Communications (Cambridge, United Kingdom), vol. 16, pp. 1432-1433.
Mohapatra et al: "Facile Synthesis of Anion Dependent Versatile CuI and Mixed-Valent Porous CuI/CuII Frameworks", 2010, Dalton Transactions, vol. 39, No. 14, pp. 3412-3419.
Nather, et al: "Synthesis, Crystal Structure and Thermal Reactivity of New Copper(I) Halide Pyrimidine-Containing Coordination Polymers", 2004, European Journal of Inorganic Chemistry, No. 14, pp. 2868-2876.
Pitteri, et al: "Displacement of Neutral Nitrogen Donors by Chloride in AuCl3(3R-py) (3R-py=meta-Substituted Pyridine): Comparison Between meta- and para-Substituted Pyridines by Kinetics and DFT Calculations", 2007, European Journal of Iinorganic Chemistry, vol. 32, pp. 5138-5143.
Prince et al: "Synthesis and Structure of (2-Amino-5-Bromopyrimidine)Bromocopper(I)", 1997, Journal of Coordination Chemistry, vol. 41, No. 4 pp. 339-345.
Rossenbeck et al: "Three-Dimensional Copper(I) Halide Based Coordination Networks with Asymmetrically Substituted Bridging N-Sonor Ligands", 1999, Zeitschrift fuer Naturforschung, vol. 54, No. 12, pp. 1510-1516.
Liu, Zhiwei et al., A Codeposition Route to CuI-Pyridine Coordination Complex for Organiz Light-Emitting Diodes, Journal of the American Chemical Society, vol. 133, No. 11, Mar. 23, 2011, 3700-3703.
Ford, Peter C. et al., Photoluminescence Properties of Multinuclear Copper(I) Compounds, Chemical Reviews, vol. 99, No. 12, Dec. 1, 1999, 3625-3648.
Kyle, Kevin R. et al., Photophysical Studies in Solution of the Tetranuclear Copper(I) Clusters Cu4I4L4 (L=Pyridine or Substitute Pyridine)1-3 Journal of the American Chemical Society, vol. 113, No. 8, Apr. 1, 1991 2954-2965.
Parmeggiani, Fabio et al., Preparation of Luminescence Thermochromism of Tetranuclear Copper(I)-Pyridine-Iodide Clusters, Journal of Chemical Education, vol. 89, No. 7, May 14, 2012, 946-949.

* cited by examiner

LIGHT EMITTING HYBRID SEMICONDUCTORS BASED ON IB-VII BINARY COMPOUNDS

CROSS-REFERENCE TO RELATED APPLICATION

The present application claims priority benefit under 35 U.S.C. § 119(e) of U.S. Patent Application Ser. No. 61/834,955 filed Jun. 14, 2013, the disclosure of which is incorporated by reference herein in its entirety.

STATEMENT REGARDING FEDERALLY FUNDED RESEARCH

This invention was made in part with government support under Grant No. DMR-1206700 awarded by the National Science Foundation. The government has certain rights in the invention.

FIELD OF THE INVENTION

The present invention relates to the field of light emitting materials, which emit strongly over the entire visible spectrum, and in particular white and yellow color, devices made therefrom, and methods of making these materials and devices.

BACKGROUND OF THE INVENTION

Concerns about global warming have led to a worldwide effort in the science community to reduce greenhouse gas emissions and to increase energy efficiency. Conservation of energy through gradual diversion of resources to renewable green energy paves the way for tomorrow's consumption and a cleaner environment. Solid-state lighting ("SSL") technology in the form of light-emitting diodes ("LEDs") generates high-efficiency light sources, converts electricity into light much more effectively than conventional lighting sources. The U.S. Department of Energy has estimated that switching to LED lighting over the next two decades could save the country $250 billion in energy costs over that period, which could reduce the electricity consumption for lighting by nearly one half, and avoid 1,800 million metric tons of carbon dioxide emission.

Low-cost and high-efficiency white light emitting diodes ("WLEDs") (144 lm/W) are considered a potential light source to replace conventional incandescent (15 lm/W) or fluorescent lighting (114 lm/W) prevalent in major infrastructures. Other applications range from computer displays to car headlights. However, major setbacks of SSL are the cost, the dependence on the rare earth ("RE") elements, which are in serious supply shortage, and the lack of their recyclability, thus causing damages to the environment. Today, the purchase price of WLED lighting products is significantly higher than that of their conventional counterparts, and the energy savings often are not enough to offset the difference within an attractive payback period.

Common approaches to produce WLEDs include blending of three primary colored LEDs, namely red, green, and blue ("RGB") diodes, or combination of a blue (or ultraviolet, UV) LED with a yellow phosphor (or multiphosphors). Either process requires complex doping/mixing and delicate control of multiple materials and colors, which proves both challenging and costly. At present, commercially available WLEDs are predominantly phosphor based (e.g., a yellow-emitting phosphor, $Ce^{3+}$ doped yttrium aluminum garnet or (YAG):$Ce^{3+}$, coupled with a blue-emitting InGaN/GaN diode). While less expensive than the RGB diodes, the (YAG):$Ce^{3+}$ type phosphors and WLEDs have issues such as unsuitability for solution process, poor color rendering index (CRI), high correlated color temperature (CCT) and dependence on rare earth (RE) component, which limit their widespread commercialization in general lighting market.

About 20 percent of global RE elements are used in clean energy technologies. Among them lanthanum, cerium, europium, terbium and yttrium are the important components used in the phosphors for energy-efficient lighting. Since the demand for RE elements as an input for different technologies is increasing, their prices have been rising constantly. Comparing to the prices in 2001 the increase level is between four to forty-nine fold in current dollars. Between 2001 and Jul. 19, 2011, the price increases of certain rare earth elements are as follows: lanthanum 3,200%, cerium 2,600%, dysprosium 4,900%, terbium 1,600%, europium 600% and yttrium 400%. (See *Critical Materials Strategy*, U.S. Department of Energy, available at http://energy.gov/sites/prod/files/DOE_CMS2011_FINAL_Full.pdf, December 2011.)

Global rare earth oxide (REO) production in 2010 was estimated to be 120,000 tones, and it is expected that the total production capacity will increase to 200,000 tons in 2015. However, the demand is much higher than the production, for example, two thirds of the global demand for europium oxide is for use in phosphors. Based on a model calculation, which assumes the limited substitution of LEDs and organic LEDs (OLEDs) for florescent lighting, production capacity has to be increased by 250 tons per year to meet 2025 demand. The estimated supply of yttrium oxide for 2005 is 11,000 tons/year while the demand can be 12,000 tons/year, assuming limited substitution of LEDs or OLEDs for florescent lighting.

The DOE's 2011 *Critical Materials Strategy* report shows that several rare earth materials that are used in clean energy technologies are at risk of supply disruptions in the short term. Use of clean technologies that are dependent on these materials may be affected by supply challenges that exist for rare earth metals, especially dysprosium, neodymium, terbium, europium and yttrium. Therefore, developing new types of phosphors, especially white/yellow phosphors and/or white/yellow light emitting semiconductor materials that are energy efficient, cost-effective, and free of RE elements is of great importance and in high demand for solid state lighting technologies.

SUMMARY OF THE INVENTION

The present invention provides a novel class of IB-VII based crystalline, inorganic-organic hybrid semiconductor materials with excellent light, especially white and yellow light, emission properties to address the foregoing need.

In one aspect, the present invention provides a IB-VII inorganic-organic hybrid semiconductor compound, formed from a Group IB transition metal halide salt and an organic heteroaryl ligand, wherein at least one ring atom of the heteroaryl ligand is a heteroatom independently selected from N, O and S and the Group IB metal is coordinated to a ring heteroatom.

According to one embodiment, a compound is provided having the formula:

wherein:
M is a Group IB transition metal ion,
X is a halide ion,

L is an organic heteroaryl ligand, wherein at least one ring atom is a heteroatom selected from N, O, or S that is coordinated to M, and n=0.5, 1, 2 or 3.

In one embodiments, the heteroaryl ligand is selected from the group consisting of pyridine (py), bipyridine (bpy), pyrimidine (pm) and pyrazine (pz), each substituted by one, two or three substituents independently selected from the group consisting of halogens, —$OR^1$, —$SR^1$, —$NO_2$, —CN and —$NR^aR^b$, wherein $R^1$ at each occurrence is independently hydrogen (H) or $C_1$-$C_4$ alkyl,—and $R^a$ and $R^b$ are independently $C_1$-$C_4$ alkyl, and wherein the Group IB metal of said halide salt is coordinated to a ring heteroatom of said heteroaryl ligand, further wherein the atoms of said compound are arranged to form a material having a 1-D, 2-D or 3-D crystalline lattice structure, wherein the MX (inorganic metal halide) of said crystalline lattice structure consists essentially of a motif of staircase chains. In one embodiment, the atoms of the inorganic-organic hybrid IB-VII semi-conductor compound are arranged to form a material having a 1-D, 2-D or 3-D crystalline lattice structure. In another embodiment, the inorganic-organic hybrid IB-VIII semiconductor material of the present invention comprises a crystalline structure formed from a plurality of recurring 1D MX(L) lattice structures, wherein the recurring 1D-MX(L) lattice structure is formed from a recurring unit of X-M-L, wherein adjacent X-M-L units are aligned antiparallel to each other so that each M of a recurring unit X-M-L coordinates with two additional X atoms of two other X-M-L units adjacent to said recurring unit, and each X of said recurring unit coordinates with two additional M atoms of said two other X-M-L units adjacent to said recurring unit, wherein the M-X portions of the recurring units form a 1D zig-zag lattice structure, and the organic ligands (L) of the recurring units coordinate to the M atoms, aligned on two opposite sides of the 1D zig-zag lattice structure. The 1D zig-zag lattice structures formed by the X-M-L molecules may optionally stack together with each other through the aligned organic ligands to form orderly 2D and 3D crystalline lattice structures.

In another embodiment, the inorganic-organic hybrid IB-VII semiconductor material of the present invention comprises a crystalline structure formed from a plurality of recurring 2D-MX(L)$_{0.5}$ lattice structures, wherein the recurring 2D-MX(L)$_{0.5}$ lattice structure is formed from a recurring unit of X-M-L$_{0.5}$, wherein adjacent X-M-L$_{0.5}$ units are aligned antiparallel to each other so that each M of a recurring unit X-M-L$_{0.5}$ coordinates with two additional X atoms of two other X-M-L$_{0.5}$ units adjacent to said recurring unit, and each X of said recurring unit coordinates with two additional M atoms of said two other X-M-L$_{0.5}$ units adjacent to said recurring unit, wherein the M-X portions of the recurring units form 1D zig-zag lattice structures, and every two adjacent 1D zig-zag lattice structures are interconnected by the shared organic ligands (L) through coordination to the M atoms in the 1D zig-zag lattice structures to form 2D lattice structures. The 2D lattice structures may optionally stack together with each other through the aligned organic ligands to form orderly 3D crystalline lattice structures.

In another aspect, the present invention provides compositions comprising an inorganic-organic hybrid IB-VII semiconductor material disclosed herein.

In another aspect, the present invention provides semiconductor devices characterized by a semiconductor die comprising an inorganic-organic hybrid IB-VII semiconductor material disclosed herein.

In another aspect, the present invention provides light-emitting diodes characterized by a semiconductor die comprising the inorganic-organic hybrid IB-VII semiconductor material disclosed herein. In one embodiment, the light emitting diode of the present invention contains the inorganic-organic hybrid IB-VII semiconductor material, or a composition thereof, coated on the semiconductor die of the device. In one embodiment, the present invention provides a light-emitting diode or a semiconductor device comprising a semiconductor die comprising an inorganic-organic hybrid IB-VII composition, said composition comprising a Group IB transition metal halide salt and an organic heteroaryl ligand, wherein said heteroaryl ligand is selected from (a) the group consisting of pyridine (py), bipyridine (bpy), pyrimidine (pm) and pyrazine (pz), each optionally substituted by one, two or three substituents independently selected from the group consisting of halogens, —$OR^1$, —$SR^1$, —$C_1$-$C_4$, alkyl, —$NO_2$, —CN and —$NR^aR^b$, wherein $R^1$ at each occurrence is independently hydrogen (H) or $C_1$-$C_4$ alkyl, and $R^a$ and $R^b$ are independently hydrogen or $C_1$-$C_4$ alkyl; or (b) the group consisting of 1,2-bis(4-pyridyl)ethane (bpe), 4,4'-dipyridyl sulfide (dps), 1,2-bis(4-pyridyl)ethene (bpee), 4,4'-dipyridyl disulfide (dpds), 1,3-bis(4-pyridyl)propane (bpp);

wherein the Group IB metal of said halide salt is coordinated to a ring heteroatom of said heteroaryl ligand to form a complex.

These and other aspects of the present invention will be described in greater detail below.

BRIEF DESCRIPTION OF THE DRAWINGS

FIGS. 1A-1C show three common types of copper iodide building motifs;

FIGS. 2A-2D show Structure plots for 0D-$Cu_2Br_2$(3,5-dmpy)$_4$ (A), 2D-$Cu_2I_2$(5-Br-pm)$_2$ (B), 0D-CuBr(3-pc)$_3$ (C) and 1D-CuBr(3-Br-py) (D);

DETAILED DESCRIPTION OF THE INVENTION

The present invention is based on the discovery of inorganic-organic IB-VII hybrid semiconductor materials (IB: Cu, Ag, Au; VII: Br, I). These materials show strong and systematically tunable band gap and optical emission properties, including white light emission, making them promising for use as alternative white phosphors or white LEDs. The inventive materials are built on environmentally friendly inorganic materials. While silver and gold can be used, commercially practical embodiments of the present invention comprise CuBr and CuI, which have sharp emissions between 400 to 450 nm, and heteroaromatic organic ligands such as pyridine (py), bipyridine (bpy) 4-cyanopyridine (4-CN-py), 3-picoline (3-CH$_3$-py), 3-bromopyridine (3-Br-py), 3-iodopyridine (3-I-py), 4-amino-5-iodopyridine (4-NH$_2$-5-I-py), 5-bromopyrimidine (5-Br-pm), and 2,6-dimethylpyrazine (2,6-(CH$_3$)$_2$-pz).

Figure 1A:
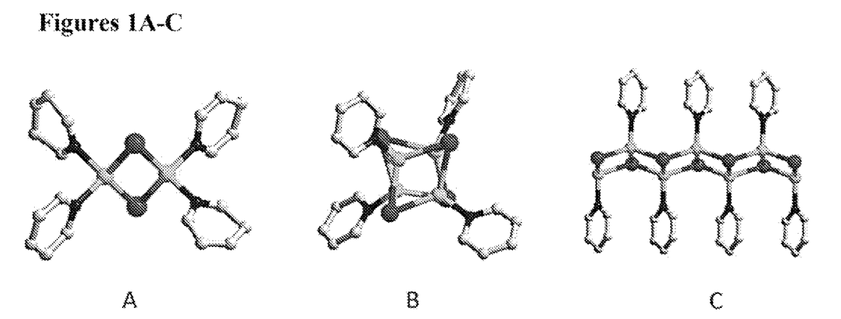

The inorganic-organic IB-VII hybrid compounds typically assemble to form one of three crystalline structural motifs of Group IB transition metal halides as shown in FIG. 1. The transition metal halide inorganic motifs are usually rhomboid dimers (FIG. 1A), cubane tetramers (FIG. 1B) or staircase chains (FIG. 1C). The organic linkers (L) are exemplified here by nitrogen-containing heteroaryl rings; however oxygen- and sulfur-containing heteroaryl counterparts, and heteroaryl rings containing combinations of N, O and S may also be used. In some embodiments, the heteroaryl ligand is selected from the group consisting of py, bpy, pm, pz, 4-Cl-py, 3-Br-py, 3-I-py, 4-NH$_2$-py, 2-Br-pm, 3-CH$_3$-py (3-picoline), and 4-CH$_3$-py (4-picoline). In some embodiments, the inorganic-organic IB-VII hybrid compound is selected from the group consisting of 1D-CuI(py), 1D-CuI(2,6-diMe-pz), 1D-CuI(pm), 1D-CuI(5-Br-pm), 1D-CuI(3-I-py), 1D-CuI(4-NH$_2$-5-I-py), 1D-CuI(3-Br-py), 1D-CuBr(py), 1D-CuBr(py), 1D-CuBr(pm), 1D-CuBr(pz), 1D-CuBr(4-Cl-py), 1D-CuBr(3-Br-py), 1D-CuBr(3-I-py), 1D-CuBr(4-NH$_2$-py), 1D-CuBr(2-Br-pm), 1D-CuBr(3-CH$_3$-py), and 1D-CuBr(4-CH$_3$-py).

Figure 2A:
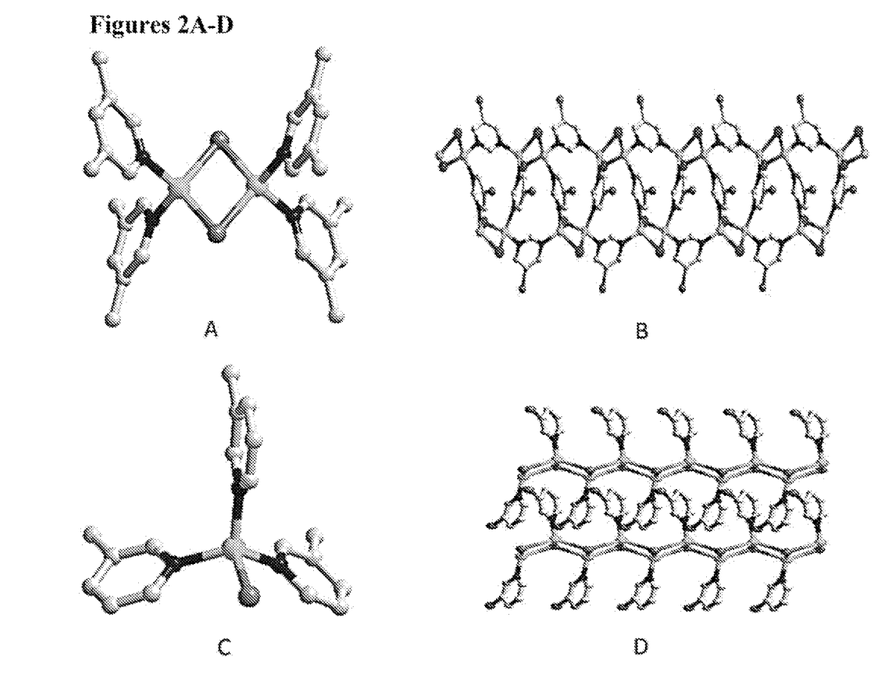

The organic linkers, either mono-N-donor or multi-N-donor (when the heteroatom is nitrogen), coordinate with the Group IB transition metal, e.g., Cu, to form molecular (0D) and one-dimensional (1D), two-dimensional (2D) or three-dimensional (3D) crystalline lattice structures (FIG. 2).

In a non-crystalline state, the materials typically emit in the UV range. When integrating the inorganic IB-VII modules and organic ligands into a single crystalline structure with coordination bonds between the copper ions and heteroatoms, e.g., nitrogen, the so-formed hybrid materials exhibit fluorescence in a broad energy range. The emissions of these hybrid materials typically fall in the visible light region, and are band gap emissions, namely, upon excitation, electrons are first excited to the conduction band, then returned to the valence band. DFT calculations reveal that the valence band of the compound mainly consists of the 3d orbitals of copper, when the transition metal is copper, and the 5p orbitals of iodine, when the halide is iodine, while the conduction band is mainly made of the 2p orbitals of carbon and nitrogen atoms, when the heteroatom is nitrogen.

These results indicate that the band gap emission involves a charge transfer between the organic molecules and inorganic component. Based on this observation, by changing the functional group (electron donating or electron withdrawing group) on the organic molecules, essentially substituting one organic molecule for another, their LUMO energy, and thereby the conduction band of the hybrid structures, can be systematically tuned to give rise to white light emission.

The organic linkers are roughly divided into four groups: pyridine (py) based, pyrimidine (pm) based, pyrazine (pz) and bipyridine (bpy) based linkers, which are summarized in Table 1:

TABLE 1

TABLE 1-continued bpy based linkers: 4,4'-bpy; 4,4'-dipyridyl sulfide (dps); 1,2-bis(4-pyridyl)ethane (bpe); 1,2-bis(4-pyridyl)ethane (bpee); 4,4'-dipyridyl disulfide (dpds); 1,3-bis(4-pyridyl)propane (bpp)

The present invention provides a series of hybrid lattice structures containing an inorganic 1D chain or 2D layer and various organic linkers. The compounds emit light of different colors under excitation by a light source such as a UV lamp.

Notably, the emission ranges of both CuI(5-Br-pm) (5-Br-pm=5-bromopyrimidine) and CuI(3-Br-py) (3-Br-py=3-bromopyridine) crystals are within white light spectrum (425-650 nm and 450-700 nm, respectively), with CIE coordinates of (0.26, 0.35) and (0.36, 0.41), respectively. In addition, high quality white light emission can be achieved by doping some of these CuX(L) (L=ligand) systems with a second ligand. One example is the doping of CuI(py) with pyrimidine (pm). Semiconductor materials according to the present invention include materials in which from about 0.00001 to about 0.99999 mole percent of the organic ligand in the composition is replaced with the second ligand, defined herein as a "dopant."

In one embodiment, from about 0.0001 to about 0.001 mole percent of the organic ligand in the composition is replaced with the second ligand. In another embodiment, from about 0.0005 to about 0.0007 mole percent of the organic ligand in the composition is replaced with the second ligand.

While the crystal structure is confirmed by PXRD to be the same as that of CuI(py), its color and emission properties are significantly different from those of both CuI(py) and CuI(pm). A well-balanced white emission spectrum is observed, with CIE coordinates of (0.31, 0.33), coincident with that of the pure white light. Similar emission spectra are also observed for CuBr-based hybrid structures. Thus, the present invention describes a new approach to designing white light emitting semiconductor bulk materials.

The inorganic-organic IB-VII hybrid semiconductor materials of the present invention are prepared by the synthesis methods described in the Examples. That is, a solution of the IB-VII semiconductor species in saturated aqueous potassium iodide is added to a solution of the organic ligand compound in an inert solvent such as acetone, ethanol, and the like. Essentially equimolar quantities of the organic and inorganic compounds are used. A less miscible solvent, such as acetonitrile, is used as an interlayer to promote crystal growth. The compounds of the present invention are prepared in an open vessel under ambient conditions or with heating within a temperature range below the boiling point of the solvent. Depending upon the reactants and reaction conditions, crystals of the inorganic-organic IB-VII hybrid semiconductor materials of the present invention form instantaneously, or within several hours or several days.

Solid products are collected by conventional means, washed free of starting materials and impurities with appropriate solvents such as alcohol-water, and then dried with an anhydrous solvent such as ethyl ether.

The compounds of the present invention may be configured into structures that are useful in the fabrication of electrical and optical devices by conventional means well known to those of ordinary skill in the art. For example, the compounds of the present invention may be formed into structures that function as quantum dots, quantum wells and quantum wires. Generally speaking, the compounds of the present invention will find applications in devices where the quantum confined structures are useful. These include, but are not limited, to interlayer dielectric devices in microelectronics, thermo-electric devices for cooling, heating and generating electricity, and quantum well laser structures useful in optoelectric devices for the generation or modulation of light radiation, including the modulation of light radiation for the transmission of information. The semiconductor compounds of the present invention may also be used in infra-red photodetectors, lasers for spectroscopic and fiber optic applications, electroluminescent lasers and electronic phosphors. In particular, the inorganic-organic hybrid compounds may be used in light-emitting devices to generate direct white light.

Light emitting diodes (LED's) based on the inorganic-organic IB-VII hybrid semiconductor materials of the present invention are prepared by substituting the inorganic-organic IB-VII hybrid semiconductor materials of the present invention for the semiconductor compounds conventionally used in the semiconductor die of an LED. That is, a semiconductor die formed from the inorganic-organic IB-VII hybrid semi-conductor material of the present invention is placed in conductive contact between an anode and a cathode within a reflective cavity. When the anode has a voltage that is more positive than its cathode by at least the LED's forward voltage drop, current flows. Electrons are excited from the valence band to the conduction band of the hybrid material and, upon return to the valence band, release energy in the form of photons.

The following non-limiting examples set forth herein below illustrate certain aspects of the invention.

EXAMPLES

A number of new $MX(L)_n$ inorganic-organic hybrid materials, where M is Cu, X=Br or I, and L is optionally substituted heteroaryl, were designed and synthesized using several synthesis methods. Their crystal structures were determined and thermal stability analyzed. The 1D-MX(L) hybrid structures display systematically tunable optical absorption and emission properties. Ligand mixing in suitable 1D-CuX(L) structures gives rise to high quality white light emission with high intensity. The current invention has achieved CIE coordinates and CRI as good as (0.31, 0.33) and 87.4, respectively.

A. Synthesis of CuI(L) Crystals (L=Organic Ligand)

Example 1. 1D-CuI(pyridine)

Single crystals of 1D-CuI(py) were grown by adding a solution of CuI (0.190 g; 1 mmol) in saturated potassium iodide solution (2 mL) to a solution of pyridine (0.079 g; 1 mmol) in acetone (2 mL). Acetonitrile (2 mL) was used as interlayer between the above two solutions to help crystal growth. The mixture was left in the solution at room temperature overnight to yield colorless crystals.

Figure 3:
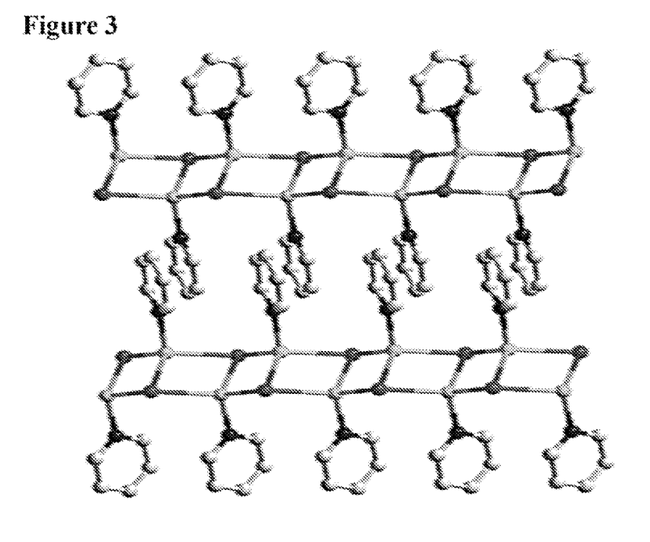
FIG. 3 illustrates the crystal structure of 1D-CuI(py)

The crystal structure of 1D-CuI(py) is composed on "ladder" shaped 1D $Cu_2I_2$ ribbons (FIG. 3). All Cu(I) atoms in the ribbon form 3 bonds to I, and all I atoms bridge to three copper metal centers. The $Cu_2I_2$ ribbon has the same atomic ratio, valence state and coordination type as its parent rock-salt (α-CuI) structure. Each pyridine molecule binds to a copper atom via its N atom to complete the fourth coordination of Cu(I), giving a stable and preferred tetrahedral geometry.

Comparison between experimental pattern of CuI(py) and simulated pattern from single crystal data show they match well. The TG analysis was performed under nitrogen atmosphere with a heating rate of 10° C./min in the temperature range 25-450° C. The TG profile shows that the sample is thermally stable up to 80° C. Above this temperature, the compound decomposes. The remaining weight (71%) is close to the percentage of CuI in the hybrid structure.

Example 2. 1D-CuI(2,6-dimethylpyrazine)

A solution of CuI (0.190 g; 1 mmol) in saturated potassium iodide solution (2 mL) was added to a solution of 2,6-dimethylpyrazine (0.108 g; 1 mmol) in acetone (2 mL). Acetonitrile (2 mL) was used as interlayer between the above two solutions to help crystal growth. The mixture was left at room temperature overnight and the resulting yellow crystals were collected after filtration.

Figure 4:
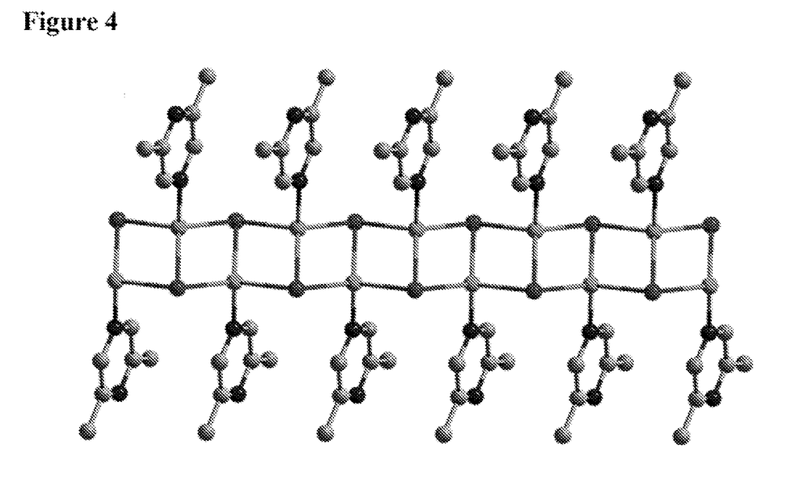
FIG. 4 illustrates the crystal structure of 1D-CuI(2,6-(CH$_3$)$_2$-pz)

The crystal structure of 1D-CuI(2,6-$(CH_3)_2$-pz) is very similar to that of 1D-CuI(py), except pyridine molecules are replaced by 2,6-dimethylpyrazine. The Cu—I distances in the $Cu_2I_2$ ribbon vary from 2.6320(7) to 2.6530(6) Å. Each 2,6-dimethylpyrazine binds to one copper atoms via one of the two N atoms, leaving the second N atom uncoordinated (FIG. 4).

Comparison between experimental and simulated X-ray diffraction patterns of 1D-CuI(2,6-$(CH_3)_2$-pz) confirms phase purity and high crystallinity of the product. The TG analysis was performed in $N_2$ atmosphere with a heating rate of 10° C./min in the temperature range 25-450° C. The TG curve of 1D-CuI(2,6-$(CH_3)_2$-pz) shows that it is thermally stable up to 100° C. Above this temperature, the structure decomposes with only CuI found as residue. The remaining weight (63%) is close to the percentage of CuI in the structure.

Example 3. 1D-CuI(5-bromopyrimidine)

Single crystals of 1D-CuI(5-Br-pm) was acquired from solution diffusion method: A solution of CuI (0.190 g; 1 mmol) in saturated potassium iodide solution (2 mL) was added with a solution of 5-bromopyrimidine (0.159 g; 1 mmol) in acetone (2 mL). 2 ml of acetonitrile was used as interlayer between the above two solutions to help crystal growth. The mixture was left at room temperature overnight and the resulting colorless crystals of 1D-CuI(5-Br-pm) were collected after filtration.

Figure 5:
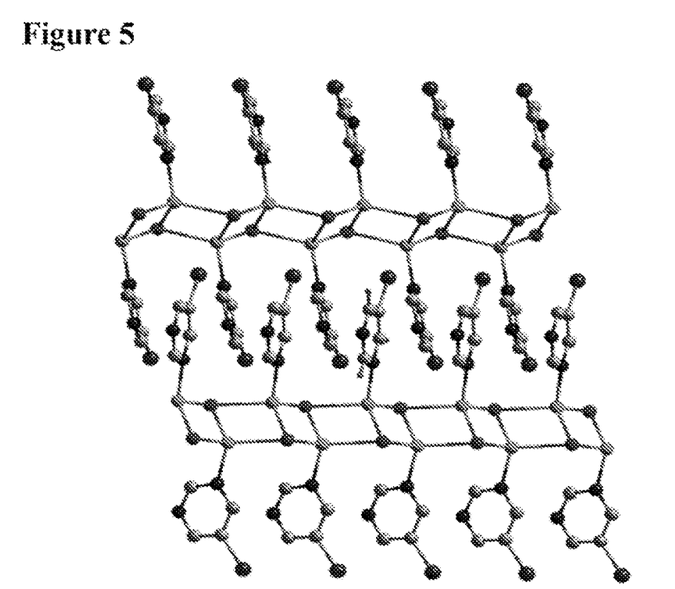
FIG. 5 illustrates the crystal structure of 1D-CuI(5-Br-pm.

Single crystal X-ray structural analysis of 1D-CuI(5-Br-pm) shows that the structure is built from one-dimensional $Cu_2I_2$ ladder. The asymmetric unit contains one crystallographically unique tetrahedral $Cu^+$ cation, one unique $I^-$ anion and one 5-bromopyrimidine ligand (FIG. 5). All Cu(I) atoms in the $Cu_2I_2$ double-stranded chains are 3-fold coordinated to $\mu_3$-$I^-$, and all $\mu_3$-$I^-$ also bridge to three copper atoms giving Cu—I distances varying from 2.607(3) to 2.675(3) Å.

A comparison between experimental and simulated X-ray diffraction patterns of the 1D-CuI(5-Br-pm) sample indicates that it is pure and highly crystalline. The TG analysis was performed under $N_2$ atmosphere with a heating rate of 10° C./min in the temperature range 25-450° C. The TG curve of 1D-CuI(5-Br-pm) shows that it is thermally stable up to 110° C. Above this temperature, the structure decomposes to CuI. The experimental weight loss (45%) is close to the theoretical percentage of 5-bromopyrimidine in the structure.

Example 4. 1D-CuI(3-iodopyridine)

Figure 6:
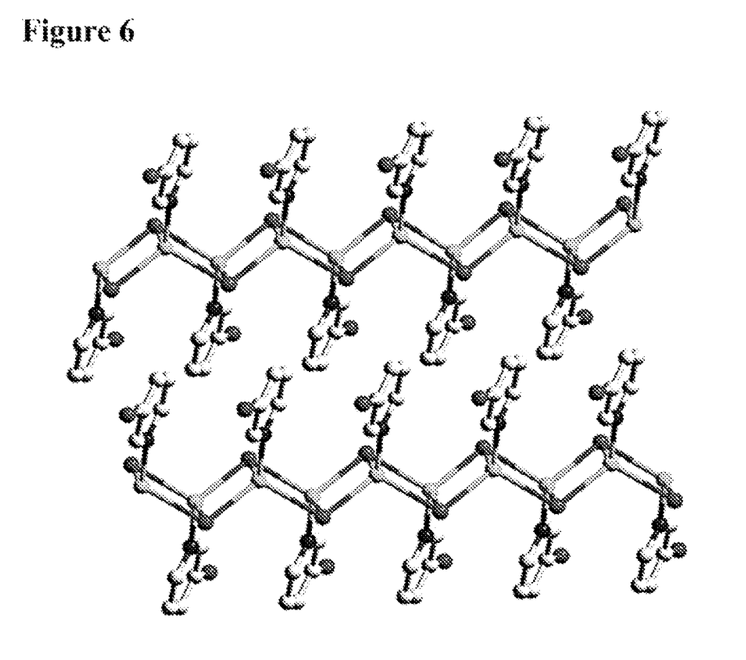
FIG. 6 illustrates the crystal structure of 1D-CuI(—I-py)

A solution of CuI (0.190 g; 1 mmol) in saturated potassium iodide solution (2 mL) was added with a solution of 3-iodopyridine (0.205 g; 1 mmol) in acetone (2 mL). Acetonitrile (2 mL) was used as interlayer. The mixture was left at room temperature overnight and the resulting colorless crystals were collected after filtration. Similar to 1D-CuI (2,6-$(CH_3)_2$-pz) and 1D-CuI(5-Br-pm), all Cu(I) atoms in the $Cu_2I_2$ ladder-like chains of 1D-CuI(3-I-py) (3-I-py=3-iodopyridine) are 3-fold coordinated to iodide, and all iodide atoms also bridge to three copper metal centers giving Cu—I distances varying from 2.6344(6) to 2.6711(7) Å (FIG. 6). The $Cu_2I_2$ ladder-like chain can also be regarded as a ribbon that is formed by connecting the two CuI zigzag single chains via Cu—I bonds.

Comparison between experimental and simulated X-ray diffraction patterns of 3D-CuI(3-I-py) confirms the pure phase of the product. The TG curve of 1D-CuI(3-I-py) shows that it is thermally stable up to 100° C. Above this temperature, the structure decomposes and only CuI remains. The remaining weight (49%) is close to the theoretical percentage of CuI in the hybrid structure.

Example 5. 1D-CuI(4-amino-5-iodopyridine)

A solution of CuI (0.190 g; 1 mmol) in saturated potassium iodide solution (2 mL) was added to a 2 mL acetonitrile and a solution of 4-amino-5-iodopyridine (0.220 g; 1 mmol)

in acetone (2 mL). The mixture was left at room temperature overnight and the resulting yellow crystals were collected after filtration.

Figure 7:
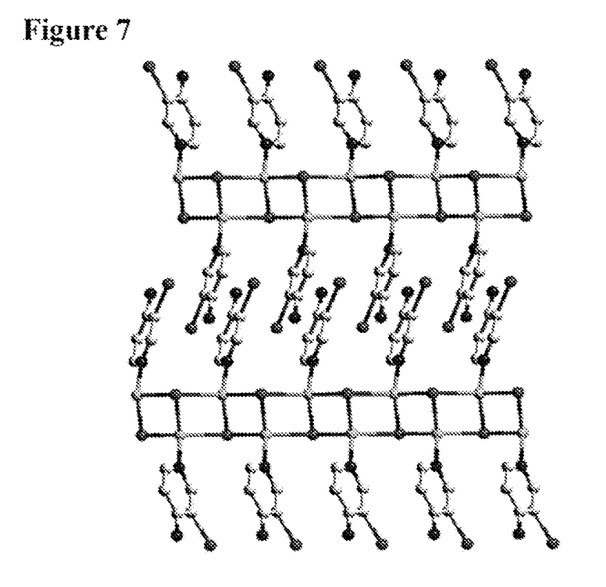
FIG. 7 illustrates the crystal structure of 1D-CuI(4-NH$_2$-5-I-py)

1D-CuI(4-NH$_2$-5-I-py) (4-NH$_2$-5-I-py=4-amino-5-iodopyridine) crystallizes in the monoclinic structure with space group C2/c. The asymmetric unit of 1D-CuI(4-NH$_2$-5-I-py) consists of one Cu, one I and one 4-amino-5-iodopyridine ligand, and each Cu$^+$ ion has a tetrahedral geometry composed of three I$^-$ ions and one N from one 4-amino-5-iodopyridine ligand (FIG. 7). The Cu—N distance is 2.031(6) Å, and Cu—I bond lengths vary from 2.6411(12) to 2.6820(13) Å. The distance between adjacent Cu ions is 2.9154(14) Å, which shows a weak Cu—Cu interaction.

The experimental and simulated X-ray diffraction patterns of the CuI(4-NH$_2$-5-I-py) indicate that the sample is of high purity and crystallinity. The TG analysis was carried out in N$_2$ gas with a heating rate of 10° C./min in the temperature range 25-450° C. The TG curve of 1D-CuI(4-NH$_2$-5-I-py) shows that it is thermally stable up to 100° C. The remaining weight (47.4%) after decomposition matches well with the theoretical percentage of CuI in the structure (FIG. 12).

Example 6. 1D-CuI(3-bromopyridine)

Pure phase of 1D-CuI(3-Br-py) powder sample was obtained from a mixture of CuI (0.019 g; 0.1 mmol), 3-bromopyridine (0.016 g; 0.1 mmol) and 3 mL acetonitrile. After leaving the mixture over night, the pure white powder of 1D-CuI(3-Br-py) was precipitated from solution and collected.

Single crystals of 1D-CuI(3-Br-py) were acquired by reaction of a solution of CuI (0.190 g; 1 mmol) in saturated potassium iodide solution (2 mL) with a solution of 3-bromopyridine (0.158 g; 1 mmol) in acetone (2 mL). Acetonitrile (2 mL) was used as the interlayer between the above two solutions. The mixture was left at room temperature overnight and the resulting colorless crystals were collected by filtration.

1D-CuI(3-Br-py) crystallizes in a monoclinic structure with space group C2/c. The asymmetric unit of 1D-CuI(3-Br-py) consists of one Cu, one I and one 3-bromopyridine ligand (FIG. 7). Each Cu$^+$ ion has a tetrahedral geometry composed of three I$^-$ ions and one N from one 3-bromopyridine ligand. The Cu—N distance is 2.055(14) Å, and Cu—I bond lengths vary from 2.607(3) to 2.675(3) Å. The distance between adjacent Cu ions ranges from 2.772(5) to 2.960(5) A°, which shows a weak Cu—Cu interaction.

Comparison between experimental and simulated X-ray diffraction patterns of 1D-CuI(3-Br-py) sample demonstrates its high crystallinity and purity. The TG analysis was performed in N$_2$ with a heating rate of 10° C./min in the temperature range 25-450° C. The TG curve of 1D-CuI(3-Br-py) shows that it is thermally stable up to 100° C. Above this temperature, the structure decomposes to give CuI. The remaining weight (37%) is similar to the percentage of CuI in the original structure.

Example 7. Doped 1D-CuI(py)$_{1-x}$(pyrimidine)$_x$ Compounds

1D-CuI(py)$_{1-x}$(pm)$_x$ powder sample was obtained by adding pyridine (0.128 g; 1.6 mmol) and pyrimidine (0.008 g; 0.1 mmol) in 3 ml of acetone drop by drop into a solution of CuI (0.19 g; 1 mmol) in 2 ml of saturated potassium iodide solution. The pure white powder of 1D-CuI(py)$_{1-x}$(pm)$_x$ immediately precipitated from solution.

Single crystals of 1D-CuI(py)$_{1-x}$(pm)$_x$ were grown when a solution of CuI (0.190 g; 1 mmol) in saturated KI solution (2 mL) was added to a solution of pyridine (0.079 g; 1 mmol) and pyrimidine (0.004 g; 0.05 mmol) in acetone (2 mL). The mixture was left in the solution at room temperature overnight resulting in colorless crystals.

Comparison between experimental PXRD pattern of 1D-CuI(py)$_{1-x}$(pm)$_x$ and simulated pattern of 1D-CuI(py) suggests that the ligand-mixed (doped) phase has the same structure as 1D-CuI(py). The TG analysis was performed under N$_2$ gas with a heating rate of 10° C./min in the temperature range 25-450° C. The TG curve of 1D-CuI(py)$_{1-x}$(pm)$_x$ sample shows that it is thermally stable up to 80° C. Above this temperature, the structure decomposes.

Example 8. 2D-CuI(pyrimidine)$_{0.5}$

Figure 8:
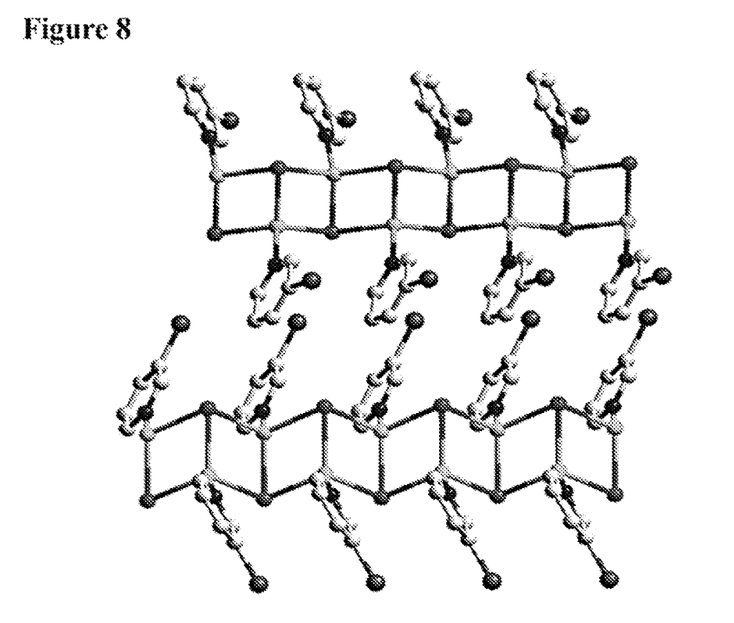
FIG. 8 illustrates the crystal structure of 1D-CuI(3-Br-py)
Figure 9:
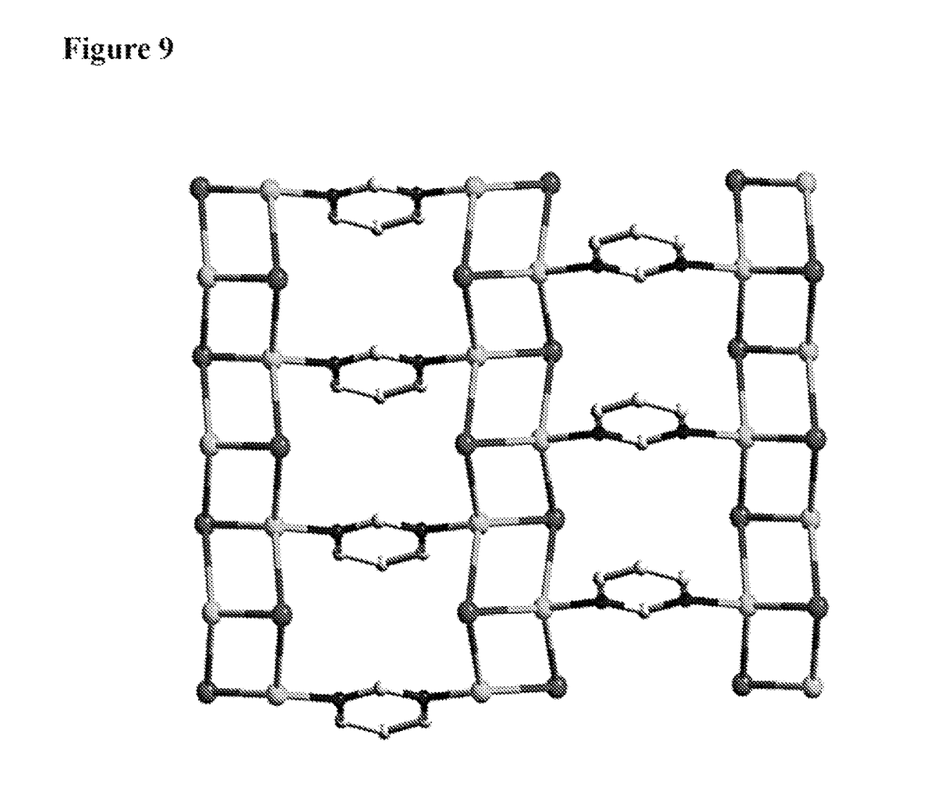
FIG. 9 illustrates the crystal structure of 2D-CuI(pm)$_{0.5}$.

Single crystals of 2D-CuI(pm)$_{0.5}$ were obtained by mixing a solution of CuI (0.190 g; 1 mmol) in saturated potassium iodide solution (2 mL) with a pyrimidine solution (0.040 g; 0.5 mmol) in acetone (2 mL). Acetonitrile (2 mL) was used as the interlayer. The mixture was left in the solution at room temperature overnight. Colorless crystals were then collected. The 2D-CuI(pm)$_{0.5}$ structure (see FIG. 8) is composed of one-dimensional (1D) CuI chains that are interconnected by the pyrimidine (pm) ligands through the two N atoms (FIG. 8). The 1D chains are very similar to those in the 1D-CuI(py) structure.

B. Synthesis of CuBr(L) Structures (L=Organic Ligand)

Example 9. 1D-CuBr(py)

Solvothermal Method:
Pyridine (70 uL; 1.0 mmol) was added to a solution of CuBr (0.144 g; 1.0 mmol) in 3.0 M potassium bromide (2.0 mL). Then the mixture was transferred to an acid digestion bomb at 80° C. for 3 days. Colorless needle like crystals were collected after washing and filtration. The yield is 87.4% based on Cu.

Diffusion Method:
Solution of pyridine (70 μL; 1.0 mmol) in ethanol (2.0 mL) was added to a solution of CuBr (0.144 g; 1.0 mmol) in 3.0 M potassium bromide (2.0 mL). To avoid quick precipitation, acetonitrile (2.0 mL) was applied as interlayer between the above two solutions to help crystal growth. The mixture was left at room temperature for three days and the resulting colorless crystals were collected after washing and filtration. The yield is 46.5% based on Cu.

Pure phase of powder sample could be obtained by adding pyridine solution into CuBr and potassium bromide solution drop by drop under magnetic stirring at room temperature. The yield is 93.3% based on Cu.

Example 10. Other 1D-CuBr(L) Phases

The similar synthesis procedures described above were applied to prepare a number of other CuBr(L) hybrid structures, including L=pm, pz, 4-Cl-py, 3-Br-py, 3-I-py, 4-NH$_2$-py, 2-Br-pm, 3-CH$_3$-py (3-picoline), and 4-CH$_3$-py (4-picoline).

Example 11. Pyrazine Doped 1D-CuBr(py)$_{1-x}$(pz)$_x$

A series of pyrazine (pz) doped CuBr(py) crystals have been synthesized by using a very small amount (less than 0.1%) of pz in the synthesis of CuBr(py) via diffusion method. A solution of 1.0 mg/mL pyrazine was made as stock solution. Calculated amount of the stock solution with pyridine in ethanol was added to CuBr and KBr solution. Acetonitrile was used as interlayer. The mixture was left at room temperature for three days and crystals were formed at the interlayer.

Example 12. 0D-$Cu_4I_4$(3,5-dmpy)$_4$ 0.191 g (1.0 mmol) CuI powder was first dissolved in 2 ml saturated KI solution. Excess 3,5-dmpy (5 mmol) was dissolve in ethanol solution. The linker solution was then added to the CuI/KI solution drop by drop in a glass vial under stirring and white precipitate would form. The product was collected by filtration and washing with ethanol. The white powder emits yellow under UV light.

Example 13. 2D-CuI(2-et-3-me-pz)$_{0.5}$

Single crystals of 2D-CuI(2-et-3-me-pz)$_{0.5}$ were obtained by slow diffusion method. The 2-ethyl-3-methyl-pz (1 mmol)/$CH_2Cl_2$ solution was slowly added to CuI (1 mmol)/saturated KI solution in a glass vial. The reaction was left without disturbance. Yellow crystals formed within a week.

Example 14. 2D-$Cu_2I_2$(5-Br-pm)$_2$

Single crystals of 2D-$Cu_2I_2$(5-Br-pm)$_2$ were obtained by slow diffusion method. The 5-Br-pm (1 mmol)/$CH_2Cl_2$ solution was slowly added to CuI (1 mmol)/acetonitrile solution in a glass vial. No precipitate was observed after the mixing. The reaction mixture was then kept undisturbed at room temperature. Red rod-like crystals formed within a week. Pure phase sample was prepared by mixing 5-Br-pm (1 mmol)/$CH_2Cl_2$ solution with CuI (1 mmol)/acetonitrile solution under stirring. Yellow precipitate formed first and turned to red after several hours. The reaction product was collected after 24 hours of stirring.

Example 15. 2D-$Cu_2I_2$(bpe)$_2$

The synthesis procedure for 2D-$Cu_2I_2$(bpe)$_2$ was modified from the method reported in Yang et al., *Inorg. Chem. Commun.*, 14, 1537 (2011). Instead of using $CuCl_2$ and high temperature, low temperature stirring method was applied. Excess bpe ligand was first dissolved in $CH_2Cl_2$ and then followed by adding CuI/acetonitrile solution under magnetic stirring. Stop adding CuI/acetonitrile solution when the precipitate formed. Adding more CuI/acetonitrile solution would lead to the formation of other type of structures. The product was collected by centrifuge and dried under vacuum.

Example 16. 2D-$Cu_2I_2$(bpp)$_2$

Pure phase sample of 2D-$Cu_2I_2$(bpp)$_2$ was obtained by modified procedure based on the method reported in Niu et al., *Eur. J. Inorg. Chem.*, 2259 (2006). Excess bpp ligand was first dissolved in $CH_2Cl_2$ under magnetic stirring followed by adding diluted CuI/acetonitrile solution drop by drop until precipitate formed. The product was collected by filtration and dried under vacuum overnight.

Example 17. 2D-$Cu_2I_2$(dps)$_2$

The crystal growth procedure was reported in Muthu et al., S.; Ni, Z.; Vittal, J. J. *Inorg. Chim. Acta.*, 358, 595 (2005). Excess dps ligand was dissolved in $CH_2Cl_2$ under magnetic stirring. Then CuI/acetonitrile solution was added drop by drop. The precipitate formed immediately. The precipitate was collected by filtration and dried in vacuum.

Example 18. 0D-$Cu_2Br_2$(3,5-dmpy)$_4$ Dimer

Single crystals of 0D-$Cu_2Br_2$(3,5-dmpy)$_4$ dimer was obtained by slow diffusion method. 3,5-dmpy was added slowly into the CuI/acetonitrile solution. Colorless crystals would form after the mixing. Pure phase sample was synthesis by mixing the excess 3,5-dimethyl-py (4 mmol)/$CH_2Cl_2$ solution with CuI (1 mmol)/acetonitrile solution. White precipitate formed after the mixing and was collected by filtration.

Example 19. 0D-CuBr(3-pcpc)$_3$

Single crystals of 0D-CuBr(3-pcpc)$_3$ were grown by slow diffusion method. 3-pc was added slowly into a CuI/acetonitrile solution. Colorless crystals were found after the mixing. Pure phased sample was obtained by adding 3-pc directly into CuI/acetonitrile solution. Precipitate formed immediately after the adding and was collected by filtration.

Example 20. 1D-CuBr(3,5-dmpy)

Single crystals of 1D-CuBr(3,5-dmpy) were acquired by layered method. The reaction was conducted in a glass vial. The bottom, middle and top layers were CuBr/saturated solution, acetonitrile, and 3,5-dmpy/ethanol solution, respectively. The crystals were formed in the middle layer. Pure phase powder sample was obtained by mixing CuBr (1 mmol)/acetonitrile solution with 3,5-dmpy (1 mmol)/$CH_2Cl_2$ solution. The white powder formed immediately after stirring. The product was collected by filtration and dried in vacuum oven.

Example 21. 1D-CuBr(3-Br-py)

Layer method was used to grow single crystals of 1D-CuBr(3-Br-py). The reaction was carried out in a glass vial. CuBr/saturated solution, acetonitrile and 3-Br-py/ethanol solution made up the bottom, middle and top layer, respectively. The crystals were formed in the middle layer. Pure phase sample was obtained by mixing CuBr (1 mmol)/acetonitrile solution with 3-Br-py (1 mmol)/$CH_2Cl_2$ solution. The white powder formed immediately after stirring. The product was collected by filtration and dried in vacuum oven.

Example 22. 1D-CuBr(3-Cl-py)

The method of Example 22 was used to synthesize 1D-CuBr(3-Cl-py) crystals, except the top layer was replaced by 3-Cl-py/ethanol solution. Pure phase sample was obtained by mixing CuBr (1 mmol)/acetonitrile solution with 3-Cl-py (1 mmol)/$CH_2Cl_2$ solution. The white powder formed immediately after stirring. The product was collected by filtration and dried in vacuum oven.

Example 23. pz Doped 1D-CuBr(Py)

$10^{-4}$ M pz ethanol solution was made as stock solution. Single crystals were obtained by layered method in test tubes or glass vials. The bottom layer was CuBr/saturated KI solution. The middle layer was acetonitrile. The top layer was the ligand/ethanol solution. The ligand/ethanol solution was made by mixing the pz stock solution with py in various molar ratios, from 0% to 1.0%. Pure phase powder samples were made by directly mixing the ligand solution with the CuBr/saturated solution under stirring at room temperature. The product was collected by filtration and dried in the vacuum oven. The PL properties at various doping levels are shown in Table 2.

TABLE 2

PL properties of pz doped 1D-CuBr(py) with various doping level.

| pz doped amount (%) | CIE | CRI | CCT (K) |
|---|---|---|---|
| 0 | 0.18, 0.32 | 42.2 | 25399 |
| 0.004 | 0.24, 0.35 | 62.5 | 10325 |
| 0.008 | 0.24, 0.35 | 63.0 | 9363 |
| 0.02 | 0.28, 0.38 | 66.2 | 7558 |
| 0.05 | 0.32, 0.41 | 68.4 | 5792 |
| 0.07 | 0.33, 0.43 | 67.0 | 5024 |
| 0.12 | 0.45, 0.42 | 97.2 | 2888 |
| 0.32 | 0.42, 0.48 | 58.0 | 3658 |

Example 24. 2D-$Cu_2Br_2$(5-Br-pm)$_2$

The synthesis of 2D-$Cu_2Br_2$(5-Br-pm)$_2$ is similar to that of 2D-$Cu_2I_2$(5-Br-pm)$_2$. Single crystals were obtained by slow diffusion method. The 5-Br-pm (1 mmol)/$CH_2Cl_2$ solution was slowly added to CuBr (1 mmol)/acetonitrile solution in a glass vial. The reaction mixture was kept undisturbed at room temperature. Red rod-like crystals formed within a week. Pure phase powder sample was prepared by mixing 5-Br-pm (1 mmol)/$CH_2Cl_2$ solution with CuBr (1 mmol)/acetonitrile solution under stirring. Yellow precipitate was observed immediately and the color turned to red after several hours. The reaction product was collected after 24 hours of stirring.

Example 25

The synthesis of the following compounds were prepared following reported procedures:
0D-$Cu_2I_2$(3,5-dmpy)$_4$—Dyason et al.; *Aust J Chem*, 37, 2201 (1984).
0D-$Cu_2I_2$(3-pc)$_4$, Rath et al., *J. Chem. Soc. Dalton*, 2449 (1986).
0D-$Cu_4I_4$(3-pc)$_4$, Cariati et al., *Chem. Mater.*, 12, 3385 (2000).
0D-$Cu_4I_4$(4-phpy)$_4$, Hu et al., *Dalton T.*, 1165 (2005).
2D-CuI(pm)$_{0.5}$, Blake et al., *Crystal Engineering*, 2, 181 (1999).
2D-CuI(2,3-dmpz)$_{0.5}$, Jess et al., *Dalton T.*, 2263 (2007).
2D-CuI(pz)$_{0.5}$, Blake et al., *Crystal Engineering*, 2, 181 (1999).
2D-CuI(4,4'-bpy)$_{0.5}$, Nather, et al., *Z Naturforsch B*, 56, 997 (2001).
2D-$Cu_2I_2$(4,4'-bpy)$_2$, Blake et al., *Crystal Engineering*, 2, 181 (1999).
1D-CuBr(py), Graham et al., *Inorg. Chem.*, 39, 5121 (2000).
2D-CuBr(pm)$_{0.5}$, Nather et al. *Z. Anorg. Allg. Chem.*, 629, 2144 (2003).
2D-CuBr(2,3-dmpz)$_{0.5}$, Graham et al., *Inorg. Chem.*, 39, 5121 (2000).
2D-CuBr(pz)$_{0.5}$, Graham et al., *Inorg. Chem.*, 39, 5121 (2000).
2D-CuBr(4,4'-bpy)$_{0.5}$, Lu et al., *J. Inorg. Chem.*, 38, 4608 (1999).
2D-$Cu_2Br_2$(bpe)$_2$, Hu et al., *Cryst. Growth. Des.*, 6, 2543 (2006).
2D-$Cu_2Br_2$(bpp)$_2$, Hu et al., *Cryst. Growth. Des.*, 6, 2543 (2006).
2D-$Cu_2Br_2$(dps)$_2$, Zhang et al., *Inorg. Chem. Commun.*, 11, 164 (2008).
2D-$Cu_2Br_2$(4,4'-bpy)$_2$, Lu et al., *J. Inorg. Chem.*, 38, 4608 (1999).

Optical Absorption Properties of 1D-CuX(L) Structures

A. 1D-CuI(L)

The optical absorption properties of the 1D-CuI(L) structures were examined and compared with those of the parent structure α-CuI. The results are summarized in Table 3. Having the same 1D chain inorganic module, the band gap of the hybrid structures can be systematically tuned from 2.2 to 3.2 eV, simply by changing organic ligands. As all compounds show band gap emission, a range of different colors are thus resulted (Table 3).

TABLE 3

Summary of absorption and fluorescent properties of CuI based hybrid structures

| Compounds | Band Gap (eV) | $\lambda_{em}$ (nm) | Emission color | QY (%) (360 nm) | QY(%) (450 nm) | Decomposition temp. (° C.) |
|---|---|---|---|---|---|---|
| 0D-$Cu_2I_2$(3,5-dmpy)$_4$ | 2.6 | 479 | Blue-green | 81.5 | 30.1 | 55 |
| 0D-$Cu_4I_4$(3,5-dmpy)$_4$ | 2.9 | 560 | Yellow | 62.9 | 6.0 | 60 |
| 0D-$Cu_2I_2$(3-pcpc)$_4$ | 2.4 | 496 | Green | 79.2 | 25.6 | 55 |
| 0D-$Cu_4I_4$(3-pcpc)$_4$ | 2.9 | 565 | Yellow | 46.3 | 4.6 | 60 |
| 0D-$Cu_4I_4$(4-phpy)$_4$ | 2.7 | 520 | Green | 74.6 | 16.3 | 100 |
| 2D-CuI(4-mepm)$_{0.5}$ | 2.7 | 490 | Green | 54.9 | 17.8 | 100 |
| 2D-CuI(pm)$_{0.5}$ | 2.5 | 505 | Green | 37.2 | 23.6 | 120 |
| 2D-CuI(2-et-3-mepz)$_{0.5}$ | 2.2 | 550 | Green-yellow | 13.8 | 9.3 | 120 |
| 2D-CuI(2,3-dmpz)$_{0.5}$ | 2.2 | 560 | Yellow | 5.8 | 5.3 | 100 |
| 2D-CuI(pz)$_{0.5}$ | 2.2 | 556 | Yellow | 13.1 | 10.2 | 140 |
| 2D-CuI(4,4'-bpy)$_{0.5}$ | 2.2 | 550 | Green-yellow | 11.4 | 12.6 | 250 |
| 2D-$Cu_2I_2$(bpe)$_2$ | 2.7 | 494 | Green | 76.5 | 6.7 | 140 |
| 2D-$Cu_2I_2$(bpp)$_2$ | 2.7 | 501 | Green | 66.0 | 10.4 | 160 |
| 2D-$Cu_2I_2$(4,4'-dps)$_2$ | 2.5 | 547 | Green-yellow | 61.8 | 41.2 | 150 |
| 2D-$Cu_2I_2$(5-Br-pm)$_2$ | 2.2 | 605 | Orange-red | 14.1 | 6.6 | 120 |
| 2D-$Cu_2I_2$(4,4'-dpy)$_2$ | 1.9 | 670 | Red | 4.4 | 2.0 | 180 |

B. 1D-CuBr(L)

The optical absorption spectra were also collected on CuBr(L) sample. The results are summarized in Table 4.

TABLE 4

Summary of absorption and fluorescent properties of CuBr based hybrid structures.

| Compounds | Band Gap (eV) | $\lambda_{em}$ (nm) | Emission color | QY (%) (360 nm) | QY(%) (450 nm) | Decomposition temp. (° C.) |
|---|---|---|---|---|---|---|
| 0D-$Cu_2Br_2$(3,5-dmpy)$_4$ | 2.8 | 510 | Green | 70.4 | 30.0 | 50 |
| 0D-CuBr(3-pcpc)$_3$ | 2.2 | 515 | Green | 95.6 | 48.8 | 50 |
| 1D-CuBr(3,5-dmpy) | 3.1 | 462 | Blue | 56.7 | 3.3 | 100 |
| 1D-CuBr(3-pcpc) | 3.0 | 478 | Blue | 51.6 | 2.1 | 100 |
| 1D-CuBr(py) | 2.8 | 482 | Blue | 32.6 | 2.5 | 120 |
| 1D-CuBr(3-Cl-py) | 2.7 | 493 | Blue-green | 21.4 | 2.1 | 100 |
| 1D-CuBr(3-Br-py) | 2.5 | 501 | Blue-green | 27.5 | 1.0 | 100 |
| 2D-CuBr(pm)$_{0.5}$ | 2.4 | 517 | Green | 23.5 | 2.5 | 120 |
| 2D-CuBr(2,3-dmpz)$_{0.5}$ | 2.3 | 573 | Yellow | 28.8 | 14.1 | 100 |
| 2D-CuBr(pz)$_{0.5}$ | 2.2 | 582 | Orange | 5.4 | 2.7 | 100 |
| 2D-CuBr(4,4'-bpy)$_{0.5}$ | 2.2 | 587 | Orange | 7.4 | 5.3 | 200 |
| 2D-$Cu_2Br_2$(bpe)$_2$ | 2.7 | 510 | Green | 30.9 | 1.0 | 120 |
| 2D-$Cu_2Br_2$(bpp)$_2$ | 2.6 | 502 | Green | 27.5 | 1.8 | 120 |
| 2D-$Cu_2Br_2$(dps)$_2$ | 2.4 | 575 | Yellow | 15.7 | 9.6 | 130 |
| 2D-$Cu_2Br_2$(5-Br-pm)$_2$ | 2.1 | 595 | Orange | 3.2 | 2.9 | 100 |
| 2D-$Cu_2Br_2$(4,4'-bpy)$_2$ | 1.9 | 680 | Red | 1.8 | 2.7 | 150 |

Optical Emission Properties of 1D-CuX(L) Structures

Four yellow-emitting phosphors that can be excited by blue light (450 nm) are listed in Table 5 with band gaps, excitation and emission wavelengths, quantum yields, and decomposition temperatures.

TABLE 5

A summary of yellow phosphors under blue excitation.

| Compound | Band gap (eV) | $\lambda_{em}$ (nm) at $\lambda_{em}$ (nm) | Excitation spectrum range (nm) | Quantum yield (%) $\lambda_{ex}$ = 450 nm | Decomposition Temp (° C.) |
|---|---|---|---|---|---|
| 2D-$Cu_2I_2$(dps)$_2$ | 2.5 | 547 | 320-470 | 41.2 | 150 |
| 1D-CuI(5-Br-pm) | 2.3 | 545 | 320-480 | 8.0 | 120 |
| 2D-CuI(pz)$_{0.5}$ | 2.5 | 556 | 450-500 | 10.2 | 120 |
| 2D-CuI(4,4'-bpy)$_{0.5}$ | 2.2 | 557 | 450-500 | 12.6 | 250 |

A. 1D-CuI(L)

Most of 1D-CuI(L) inorganic-organic hybrid compounds are luminescence active. Generally, structures made of ligands with bromo group such as 3-bromopyridine and 5-bromopyrimidine show broad emission. Both the CuI(3-Br-py) and CuI(5-Br-pm) display double peaks spanning more than 250 nm out of 300 nm in the visible light range (400-700 nm, FIG. 1). The CIE coordinates are (0.26, 0.35) for CuI(Br-py) and (0.36, 0.41) for CuI(5-Br-pm), respectively (FIG. 1). These results indicate the emission color of these two compounds is already within white light. The quantum yield of this compound is about 17%.

While both bromo-containing CuI(L) compounds emit within white light region, the color quality (CIE, CCT and CRI) is relatively poor. CuI(L) structures with mixed ligands were synthesized. CuI(py) was chosen as the primary structure and pm as dopant. CuI(py) and CuI(pm) have a 0.3 eV difference in their band gaps. This difference is due to the energy of their LUMO orbital. There are two electron withdrawing nitrogen atoms in the aromatic ring of pyrimidine compared to one nitrogen atom in pyridine. Therefore the LUMO orbital of pyrimidine is lower than that of pyridine. Their emission maxima of the two are at ~440 and 510 nm, respectively. For CuI(py)$_{1-x}$(pm)$_x$, the absorption spectrum is very similar to that of CuI(py), and the emission spectrum clearly reflects a combination of spectra of the individual parent compounds, with an additional tail at lower energy region (~570-700 nm. This gives rise to an overall well-balanced white light mission, with optimal CIE coordinates of (0.31, 0.33), coincident with that of pure white light. The Color Rendering Index (CRI) and Correlated Color Temperature (CCT) of this compound are 87.4 and 6455 K. The pyrazine doped samples also emit strongly in white-light region.

B. 1D-CuBr(L)

By doping 1D-CuBr(py) with pyrazine, white light emission was achieved, similar to what was observed for the CuI(L) systems. The doped samples (~0.05%, 0.07% and 0.09% of pyrazine to pyridine by mole) have an obvious color change from colorless to yellowish while their PXRD patterns and optical absorption spectra remain the same as undoped CuBr(py) parent structure. Both samples with 0.05% and 0.07% dopant exhibit well-balanced white light emission with high intensity. The doped CuBr(py) have significantly enhanced emission compared to their CuI(py) analogues. The CIE coordinates, color rendering index (CRI) and correlated color temperature (CCT) of the 0.07% doped sample are (0.30, 0.42), 68.5 and 4922 K, respectively.

Crystal Structure Analysis

Several crystal structures were solved by single crystal diffraction and the data are listed in Table 6. 2D-$Cu_2I_2$(5-Br-pm)$_2$ and 2D-$Cu_2Br_2$(5-Br-pm)$_2$ are 2D structures built on $Cu_2I_2$ ($Cu_2Br_2$) dimers interconencted by 5-Br-pm. Each Cu is coordinated with two nitrogen and two I (Br) atoms to build a 2D network. 0D-$Cu_2Br_2$(3,5-d)$_4$ is a molecular dimer built by 3,5-dmpy ligand. 0D-CuBr(3-pc)$_3$ is another type of molecular species, which each copper is coordinate with three nitrogen and one I atom, with the CuI to lig-and ratio of 1:3. 1D-CuI(L) is built by staircase chain and monodentate linker. Each Cu coordinates with one nitrogen and three I atoms. Their structures are shown in FIG. 2.

TABLE 6

Summary of crystal data.

| Empirical Formula | 2D-Cu₂I₂ (5-Br-pm)₂ | 0D-Cu₂Br₂ (3,5-dmpy)₄ | 0D-CuBr (3-pcpc)₃ | 1D-CuBr (3,5-dmpy) | 1D-CuBr (3-Br-py) | 1D-CuBr (3-Cl-py) | 2D-Cu₂Br₂ (5-Br-pm)₂ |
|---|---|---|---|---|---|---|---|
| Fw | 349.43 | 357.75 | 422.82 | 250.60 | 301.45 | 256.99 | 302.44 |
| Space Group | Cmca | P 21/n | R 3 m | P1 | P 21/n | P 21/c | Pbcn |
| a (Å) | 8.437(2) | 17.815(3) | 14.535(6) | 8.058(7) | 8.720(9) | 8.7438(19) | 16.1765(16) |
| b (Å) | 21.875(6) | 9.285(2) | 14.535(6) | 10.159(9) | 3.933(4) | 3.9296(9) | 8.3154(8) |
| c (Å) | 16.757(4) | 20.324(6) | 7.547(3) | 10.209(9) | 21.11(2) | 21.002(5) | 21.382(2) |
| Alpha (°) | 90.00 | 90.00 | 90.00 | 95.215(16) | 90.00 | 90.00 | 90.00 |
| Beta (°) | 90.00 | 114.225(5) | 90.00 | 96.308(15) | 100.603(13) | 100.837(3) | 90.00 |
| Gamma (°) | 90.00 | 90.00 | 120.00 | 96.396(14) | 90.00 | 90.00 | 90.00 |
| V (Å³) | 3092.6(14) | 3065.9(12) | 1380.9(9) | 821.0(13) | 711.6(12) | 708.8(3) | 2876.2(5) |
| Z | 16 | 8 | 6 | 2 | 2 | 2 | 4 |
| T (K) | 293(2) | 293(2) | 293(2) | 293(2) | 293(2) | 293(2) | 293(2) |
| λ (Å) | 0.71073 | 0.71073 | 0.71073 | 0.71073 | 0.71073 | 0.71073 | 0.71073 |
| ρ (g · cm⁻²) | 3.002 | 1.550 | 1.525 | 2.028 | 2.814 | 3.054 | 2.794 |
| Rwp | 0.0471 | 0.0429 | 0.0498 | 0.0688 | 0.0411 | 0.0756 | 0.0413 |
| Rp | 0.0265 | 0.0639 | 0.0406 | 0.0738 | 0.0519 | 0.0326 | 0.0262 |

It will be understood by those of skill in the art that numerous and various modifications can be made without departing from the spirit of the present invention. Therefore, it should be understood that the various embodiments of the present invention described herein are illustrative only and not intended to limit the scope of the present invention.

The invention claimed is:

1. A light-emitting diode or a semiconductor device comprising a semiconductor die comprising an inorganic-organic hybrid IB-VII composition, said composition comprising a Group IB transition metal halide salt and an organic heteroaryl ligand, wherein said heteroaryl ligand is selected from
   (a) the group consisting of pyridine (py), bipyridine (bpy), pyrimidine (pm) and pyrazine (pz), each optionally substituted by one, two or three substituents independently selected from the group consisting of halogens, —OR¹, —SR¹, —C₁-C₄ alkyl, —NO₂, —CN and —NRᵃRᵇ, wherein R¹ at each occurrence is independently hydrogen (H) or C₁-C₄ alkyl, and Rᵃ and Rᵇ are independently hydrogen or C₁-C₄ alkyl; or
   (b) the group consisting of 1,2-bis(4-pyridyl)ethane (bpe), 4,4'-dipyridyl sulfide (dps), 1,2-bis(4-pyridyl)ethene (bpee), 4,4'-dipyridyl disulfide (dpds), 1,3-bis(4-pyridyl)propane (bpp);
   wherein the Group IB metal of said halide salt is coordinated to a ring heteroatom of said heteroaryl ligand to form a complex.

2. The light-emitting diode or a semiconductor device of claim 1, wherein said complex has the formula:

MX(L)<sub>n</sub> wherein:
M is said Group IB transition metal,
X is a halogen,
L is said organic heteroaryl ligand having a ring heteroatom coordinated to M, and n=0.5, 1, 2 or 3.

3. The light-emitting diode or a semiconductor device of claim 1, wherein the atoms of said complex are arranged to form a material having a 1-D, 2-D or 3-D crystalline lattice structure.

4. The light-emitting diode or a semiconductor device of claim 3, wherein the inorganic metal halide motifs of the crystalline lattice structure of said material consist essentially of a motif selected from the group consisting of rhomboid dimers, cubane tetramers and staircase chains.

5. The light-emitting diode or a semiconductor device of claim 2, wherein n=1 and said crystalline structure is formed from a plurality of recur-ring 1-D MX(L) lattice structures, wherein said recurring 1D-MX(L) structure is formed from a recurring unit of X-M-L, wherein adjacent X-M-L units are aligned antiparallel to each other so that each M of a recurring unit X-M-L coordinates with two additional X atoms of two other X-M-L units adjacent to said recurring unit, and each X of said recurring unit coordinates with two additional M atoms of said two other X-M-L units adjacent to said recurring unit, wherein the M-X portions of the recurring units form 1D zig-zag structures, and the organic ligands (L) of the recurring units coordinate to the M atoms, aligned on two opposite sides of the 1D zig-zag structures.

6. The light-emitting diode or a semiconductor device of claim 5, wherein said 1D zig-zag lattice structures stack together with each other through the aligned organic ligands to form orderly 2D and/or 3D crystalline lattice structures.

7. The light-emitting diode or a semiconductor device of claim 2, wherein n=0.5 and said crystalline structure is formed from a plurality of recurring 2D-MX(L)₀.₅ lattice structures, wherein said recurring 2D-MX(L)₀.₅ structure is formed from a recurring unit of X-M-L₀.₅, wherein adjacent X-M-L₀.₅ units are aligned antiparallel to each other so that each M of a recurring unit X-M-L₀.₅ coordinates with two additional X atoms of two other X-M-L₀.₅ units adjacent to said recurring unit, and each X of said recurring unit coordinates with two additional M atoms of said two other X-M-L₀.₅ units adjacent to said recurring unit, wherein the M-X portions of the recurring units form 1D zig-zag structures, and every two adjacent 1D zig-zag lattice structures are interconnected by the shared organic ligands (L) through coordination to the M atoms in the 1D zig-zag structures to form 2D lattice structures.

8. The light-emitting diode or a semiconductor device of claim 7, wherein said 2D zig-zag lattice structures stack together with each other through the aligned organic ligands to form orderly 3D crystalline lattice structures.

9. The light-emitting diode or a semiconductor device of claim 2, wherein M is Cu, X is Br or I.

10. The light-emitting diode or a semiconductor device of claim 2, wherein L is selected from the group consisting of 4-Cl-py, 3-Br-py, 3-I-py, 4-NH₂-py, 2-Br-pm, 3-CH₃-py (3-picoline), and 4-CH₃-py (4-picoline).

11. The light-emitting diode or the semiconductor device of claim 1, wherein said complex is selected from the group consisting of 1D-CuI(py), 1D-CuI(2,6-diMe-pz), 1D-CuI(pm), 1D-CuI(5-Br-pm), 1D-CuI(3-I-py), 1D-CuI(4-NH$_2$-5-I-py), 1D-CuI(3-Br-py), 1D-CuBr(py), 1D-CuBr(py), 1D-CuBr(pm), 1D-CuBr(pz), 1D-CuBr(4-Cl-py), 1D-CuBr(3-Br-py), 1D-CuBr(3-I-py), 1D-CuBr(4-NH$_2$-py), 1D-CuBr(2-Br-pm), 1D-CuBr(3-CH$_3$-py), and 1D-CuBr(4-CH$_3$-py).

12. The light-emitting diode or a semiconductor device of claim 1, wherein the complex is further doped with a second organic ligand.

13. The light-emitting diode or a semiconductor device of claim 12, wherein said complex has formula CuX(L$^1$)$_{1-x}$(L$^2$)$_x$, wherein L$^1$ and L$^2$ are different and are independently selected from the group consisting of py, bpy, pm, pz, 4-Cl-py, 3-Br-py, 3-I-py, 4-NH$_2$-py, 2-Br-pm, 3-CH$_3$-py (3-picoline) and 4-CH$_3$-py (4-picoline), wherein x is a number in the range from about 0.00001 to about 0.99999.

14. The light-emitting diode or a semiconductor device of claim 13, wherein x is 0.0005 to 0.0007.

15. An inorganic-organic hybrid IB-VII complex, which is selected from the group consisting of 1D-CuI(5-Br-pm), 1D-CuI(3-I-py), 1D-CuI(3-Br-py), 1D-CuBr(4-Cl-py), 1D-CuBr(3-Br-py), and 1D-CuBr(2-Br-pm).

16. An inorganic-organic hybrid IB-VII complex of formula CuX(L$^1$)$_{1-x}$(L$^2$)$_x$, comprising a Group IB transition metal halide salt CuX, a first ligand L$^1$ and a second ligand L$^2$, wherein L$^1$ and L$^2$ are different and are independently selected from the group consisting of py, bpy, pm, pz, 4-Cl-py, 3-Br-py, 3-I-py, 4-NH$_2$-py, 2-Br-pm, 3-CH$_3$-py (3-picoline) and 4-CH$_3$-py (4-picoline), wherein x is a number in the range from about 0.00001 to about 0.99999.

17. The inorganic-organic hybrid IB-VII complex of claim 16, which is selected from 1D-CuI(py)$_{1-x}$(pyrimidine)$_x$ and 1D-CuBr(py)$_{1-x}$(pz)$_x$.

* * * * *